United States Patent
Accomazzi et al.

(10) Patent No.: US 11,538,578 B1
(45) Date of Patent: Dec. 27, 2022

(54) METHODS AND SYSTEMS FOR THE EFFICIENT ACQUISITION, CONVERSION, AND DISPLAY OF PATHOLOGY IMAGES

(71) Applicant: International Medical Solutions, Inc., Mississauga (CA)

(72) Inventors: Vittorio Accomazzi, Toronto (CA); Vernon Colaco, Mission Viejo, CA (US)

(*) Notice: Subject to any disclaimer, the term of this patent is extended or adjusted under 35 U.S.C. 154(b) by 0 days.

(21) Appl. No.: 17/456,868

(22) Filed: Nov. 29, 2021

Related U.S. Application Data

(60) Provisional application No. 63/261,520, filed on Sep. 23, 2021.

(51) Int. Cl.
*G16H 30/40* (2018.01)
*G06F 16/957* (2019.01)
(Continued)

(52) U.S. Cl.
CPC ........... *G16H 30/40* (2018.01); *G06F 16/957* (2019.01); *G06T 3/4053* (2013.01); *G16H 30/20* (2018.01)

(58) Field of Classification Search
CPC ...... G16H 30/40; G16H 30/20; G06F 16/957; G06T 3/4053
See application file for complete search history.

(56) References Cited

U.S. PATENT DOCUMENTS 6,711,297 B1 * 3/2004 Chang ................. G06T 1/00 382/233
8,391,574 B2 3/2013 Collins
(Continued)

FOREIGN PATENT DOCUMENTS

CA 2697596 A1 9/2010
CA 3044060 A1 5/2018
(Continued)

OTHER PUBLICATIONS

Yang et al, ("Pathology-Centric medical image retrieval with hierarchical contextual spatial descriptor", 2013 IEEE 10th International Symposium on Biomedical Imaging, San Francisco, CA, USA, Apr. 7-11, 2013) (Year: 2013).*
(Continued)

*Primary Examiner* — Amara Abdi
(74) *Attorney, Agent, or Firm* — Novel IP

(57) ABSTRACT

A method for viewing pathology images in a web browser is provided. The method includes obtaining a pathology image in a first format, converting the pathology image into a pyramid representation file comprising images grouped into a plurality of levels, wherein the images in the different plurality of levels correspond to portions of the pathology image at a same or different degrees of resolution, and wherein the images are in the first format, storing the pyramid representation file in the first memory, receiving a request from a user to view the pathology image at a specified resolution, loading one or more images from at least one of the plurality of levels corresponding to the specified resolution, wherein the one or more images are in the first format and wherein the one or more images are loaded into a web browser coupled with the first memory, converting the images into a second format such that the images' degrees of resolution are maintained, and storing the images in the second format in a second memory.

30 Claims, 5 Drawing Sheets

(51) Int. Cl.
*G06T 3/40* (2006.01)
*G16H 30/20* (2018.01)

(56) References Cited

U.S. PATENT DOCUMENTS

| | | |
|---|---|---|
| 8,659,645 B2 | 2/2014 | Tsukagoshi |
| 8,774,560 B2 | 7/2014 | Sugaya |
| 9,298,730 B2 | 3/2016 | Colaco |
| 9,310,981 B2 | 4/2016 | Lynch |
| 9,532,756 B2 | 1/2017 | Wakai |
| 9,659,030 B2 | 5/2017 | Colaco |
| 9,668,699 B2 | 6/2017 | Georgescu |
| 9,769,599 B2 | 9/2017 | Coutinho |
| 9,891,784 B2 | 2/2018 | Lee |
| 9,947,090 B2 | 4/2018 | Agam |
| 9,947,102 B2 | 4/2018 | Xu |
| 9,953,136 B2 | 4/2018 | Dorn |
| 10,127,659 B2 | 11/2018 | Hsieh |
| 10,127,662 B1 | 11/2018 | Reicher |
| 10,169,534 B2 | 1/2019 | Day |
| 10,380,735 B2 | 8/2019 | Wiemker |
| 10,460,214 B2 | 10/2019 | Lu |
| 10,579,363 B2 | 3/2020 | Kludy |
| 10,579,877 B2 | 3/2020 | Guttmann |
| 10,586,398 B2 | 3/2020 | Wenzel |
| 2003/0025694 A1 | 2/2003 | Davis |
| 2005/0021795 A1 | 1/2005 | Kuroshima |
| 2005/0102315 A1 | 5/2005 | Krishnan |
| 2007/0276214 A1 | 11/2007 | Dachille |
| 2010/0077358 A1 | 3/2010 | Sugaya |
| 2011/0067022 A1 | 3/2011 | Williams |
| 2012/0084350 A1 | 4/2012 | Xie |
| 2014/0074913 A1 | 3/2014 | Claydon |
| 2014/0108967 A1 | 4/2014 | Markham |
| 2014/0115020 A1 | 4/2014 | Colaco |
| 2014/0270432 A1* | 9/2014 | Xu ................ G06F 16/583 |
| | | 382/128 |
| 2015/0379209 A1 | 12/2015 | Kusuma |
| 2016/0071264 A1 | 3/2016 | Agam |
| 2016/0154941 A1 | 6/2016 | Laborde |
| 2016/0239615 A1 | 8/2016 | Dorn |
| 2016/0283085 A1 | 9/2016 | Beausoleil |
| 2017/0038951 A1 | 2/2017 | Reicher |
| 2017/0147545 A1 | 5/2017 | Amoli |
| 2017/0168692 A1 | 6/2017 | Chandra |
| 2018/0060512 A1 | 3/2018 | Sorenson |
| 2018/0082487 A1 | 3/2018 | Kiraly |
| 2018/0322254 A1 | 11/2018 | Smurro |
| 2018/0349724 A1 | 12/2018 | Xiang |
| 2019/0065763 A1 | 2/2019 | Berg |
| 2019/0125298 A1 | 5/2019 | Abolmaesumi |
| 2019/0130576 A1 | 5/2019 | Wu |
| 2019/0172581 A1 | 6/2019 | Zlotnick |
| 2019/0304590 A1 | 10/2019 | Wilson |
| 2019/0340752 A1 | 11/2019 | Brestel |
| 2019/0340753 A1 | 11/2019 | Brestel |
| 2019/0378341 A1 | 12/2019 | Xie |
| 2019/0394276 A1 | 12/2019 | Dachille |
| 2020/0167149 A1 | 5/2020 | Kludy |
| 2021/0358596 A1* | 11/2021 | Boda ................ G06F 3/0631 |

FOREIGN PATENT DOCUMENTS

| | | |
|---|---|---|
| EP | 2735982 A1 | 5/2014 |
| EP | 2815372 B1 | 4/2018 |
| WO | 2017011337 A1 | 1/2017 |
| WO | 2018208323 A1 | 11/2018 |
| WO | 2020212762 A2 | 10/2020 |

OTHER PUBLICATIONS

International Search Report and Written Opinion for PCT/IB2020/000381, dated Oct. 9, 2020.
International Preliminary Report on Patentability for PCT/IB2020/000381, dated Oct. 28, 2021.

* cited by examiner

METHODS AND SYSTEMS FOR THE EFFICIENT ACQUISITION, CONVERSION, AND DISPLAY OF PATHOLOGY IMAGES

CROSS-REFERENCE

The present application relies on U.S. Patent Provisional Application No. 63/261,520 filed on Sep. 23, 2021 and entitled "System and Method for Viewing Pathology Images". The '520 application is hereby incorporated by reference.

FIELD

The present specification relates generally to a system and method for facilitating the storage, retrieval and viewing of large medical images. More particularly the present specification relates to the storage, retrieval and viewing of pathology images.

BACKGROUND

Pathology is a branch of medical science that inquires into the cause, origin, and nature of disease. Pathology involves the examination of tissues, organs, and bodily fluids and also autopsies in order to study and diagnose disease. Usually a pathologist slices a tissue block into very thin layers, that are placed on a glass slide and examined under a microscope. This allows the pathologist to analyze the diseased tissue, generate a diagnosis of the disease or other conditions associated with that tissue, and author gross or microscopic descriptions of biopsy or cytology specimens.

Pathologists often need to store the original slides for future reference. However, the specimen storage process is expensive, usually requiring accessibility, cleaning, and protection, which entails greater care by specialized staff. In contrast, digital storage and distribution methods reduce these costs, increases the throughput of pathology laboratories, and enables the sharing of pathology images for analysis. Furthermore, despite using very methodical analytic workflows, it is possible for the same pathologist to draw different conclusions about the same specimen at different times. Consequently, there is the requirement for enabling second opinions from different pathologists regarding each sample.

Digital pathology comprises the digital capture of an image from a classic glass slide as well as management of the associated data. In digital pathology, glass slides are converted into digital slides that can be viewed, managed, shared, and analyzed on a computer, is a sub-field of pathology that focuses on data management based on information generated from digitized specimen slides. Accordingly, it is preferred to digitally capture the slide images, store those images, and enable those images to be widely shared. Usually, Digital Slide Scanners (DSS) are used to obtain a digital image of a pathological specimen in a whole-slide images (WSI) format. As the name suggests, these images capture the slide as a whole, rather than specific artifacts found by pathologists. The WSI images made by digitized microscope slides at diagnostic resolution are very large. A typical slide scanned at ×40 (approx. 1600 megapixels) produces a file that, even when compressed, requires 2-3 gigabytes of memory and necessitates a viewer application with special functionality to accommodate a pathologist's needs. Since, pathology images are extremely large, wherein each image ranges from 3 GB to 5 GB, as compared to radiology images which range from 512 KB to 100 MB, there is need for a system and method to enable pathologists to be able to rapidly access a low resolution version of a pathology image but to also be able to then zoom into selected regions of interest in the image at higher resolutions.

There is also a need to configure pathology slides so that they can be managed in systems that use the more common DICOM imaging format. DICOM, or Digital Imaging and Communications in Medicine, is a standard for handling, storing, printing, and transmitting information in medical imaging. It includes a file format definition and a network communications protocol. DICOM enables the integration of scanners, servers, workstations, printers, and network hardware from multiple manufacturers into a picture archiving and communication system (PACS). Different devices come with DICOM conformance statements that identify which DICOM classes they support. DICOM has been widely adopted by hospitals and is making inroads in smaller applications like dentists' and doctors' offices. Preferably, pathology images would be made compatible with PACS in order to enable the easy viewing of large pathology images on web browsers along with providing zooming and panning functionality.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a system adapted to enable a user to view one or more pathology images in a web browser, wherein the system comprises: one or more web servers, wherein the one or more web servers is configured to: obtain at least one of the one or more pathology images in a first format; convert the pathology image into a file comprising images grouped into a plurality of levels, wherein the images in different ones of the plurality of levels correspond to a portion of the pathology image at a different degree of resolution, wherein each image in a given one of the plurality of levels corresponds to a portion of the pathology image at a same degree of resolution, and wherein the images are in a second format; cause the file to be stored in a first memory; convert the images into a third format; and cause the images to be stored in the third format in a second memory; and a plurality of programmatic instructions adapted to be stored in non-transient memory and executed on a client device, wherein, when executed, the plurality of programmatic instructions are adapted to receive a request from the user to view the pathology image and load one or more of the images from at least one of the plurality of levels corresponding to a specified resolution and wherein the one or more images are in the second format.

Optionally, the file is in a hierarchical representation.

Optionally, the file is in a pyramid representation.

Optionally, the one or more web servers is configured to convert the images into a third format such that the images' degrees of resolution are maintained.

Optionally, the plurality of programmatic instructions are adapted to receive the request identifying the specified resolution.

Optionally, the first memory comprises a web cache in the client device.

Optionally, the second memory comprises a web archive.

Optionally, the first format is a WSI format.

Optionally, the second format is at least one of a TIFF format, a JPEG format, or a PNG format.

Optionally, the third format is a DICOM format.

Optionally, the file is in a pyramid representation wherein a number of the plurality of levels in the pyramid representation file is at least two.

Optionally, the file is in a pyramid representation wherein a number of the plurality of levels in the pyramid representation file is no greater than one hundred.

Optionally, the file is in a pyramid representation wherein a top of the plurality of levels in the pyramid representation file comprises the pathology image at a lowest resolution.

Optionally, the file is in a pyramid representation wherein a base of the plurality of levels in the pyramid representation file comprises the pathology image at a highest resolution.

Optionally, the client device is remote from the one or more web servers.

Optionally, the third format is different from the second format and the first format.

Optionally, the second format is different from the third format and the first format.

Optionally, each of the first format, second format and third format is different from each other.

Optionally, the plurality of programmatic instructions are adapted to load the one or more images into the web browser.

Optionally, the web browser is coupled with the first memory.

In some embodiments, the present specification discloses a method for viewing pathology images in a web browser, the method comprising: obtaining a pathology image in a first format; converting the pathology image into a pyramid representation file comprising images grouped into a plurality of levels, wherein the images in different ones of the plurality of levels correspond to a portion of the pathology image at a different degree of resolution, wherein each image in a given one of the plurality of levels corresponds to a portion of the pathology image at a same degree of resolution, and wherein the images are in a second format; storing the pyramid representation file in a first memory; receiving a request from a user to view the pathology image at a specified resolution; loading one or more images from at least one of the plurality of levels corresponding to the specified resolution, wherein the one or more images are in the second format and wherein the one or more images are loaded into a web browser coupled with the first memory; converting the images into a third format such that the images' degrees of resolution are maintained; and storing the images in the third format in a second memory.

Optionally, the first memory comprises a web cache. Optionally, the second memory comprises a web archive.

Optionally, the first format is a WSI format. Optionally, the second format is at least one of a TIFF format, a JPEG format or a PNG format. Optionally, the third format is a DICOM format.

Optionally, a number of the plurality of levels in the pyramid representation file is at least two. Optionally, a number of the plurality of levels in the pyramid representation file is no greater than one hundred. Optionally, a top of the plurality of levels in the pyramid representation file comprises the pathology image at a lowest resolution. Optionally, a base of the plurality of levels in the pyramid representation file comprises the pathology image at a highest resolution.

In some embodiments, the present specification is directed towards a system adapted to enable users to view pathology images in a web browser, the system comprising: one or more web servers, wherein the one or more web servers is configured to: obtain a pathology image in a first format; convert the pathology image into a pyramid representation file comprising images grouped into a plurality of levels, wherein the images in different ones of the plurality of levels correspond to a portion of the pathology image at a different degree of resolution, wherein each image in a given one of the plurality of levels corresponds to a portion of the pathology image at a same degree of resolution, and wherein the images are in a second format; store the pyramid representation file in a first memory; convert the images into a third format such that the images' degrees of resolution are maintained; and store the images in the third format in a second memory; and a plurality of programmatic instructions adapted to be stored in non-transient memory and executed on a client device remote from the one or more web servers, wherein, when executed, the plurality of programmatic instructions are adapted to receive a request from a user to view the pathology image at a specified resolution and load one or more images from at least one of the plurality of levels corresponding to the specified resolution, wherein the one or more images are in the second format and wherein the one or more images are loaded into a web browser coupled with the first memory.

Optionally, the first memory comprises a web cache. Optionally, the second memory comprises a web archive.

Optionally, the first format is a WSI format. Optionally, the second format is at least one of a TIFF format, JPEG format, or PNG format. Optionally, the third format is a DICOM format.

Optionally, a number of the plurality of levels in the pyramid representation file is at least two. Optionally, a number of the plurality of levels in the pyramid representation file is no greater than one hundred. Optionally, a top of the plurality of levels in the pyramid representation file comprises the pathology image at a lowest resolution. Optionally, a base of the plurality of levels in the pyramid representation file comprises the pathology image at a highest resolution.

The aforementioned and other embodiments of the present specification shall be described in greater depth in the drawings and detailed description provided below.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Figure 1:
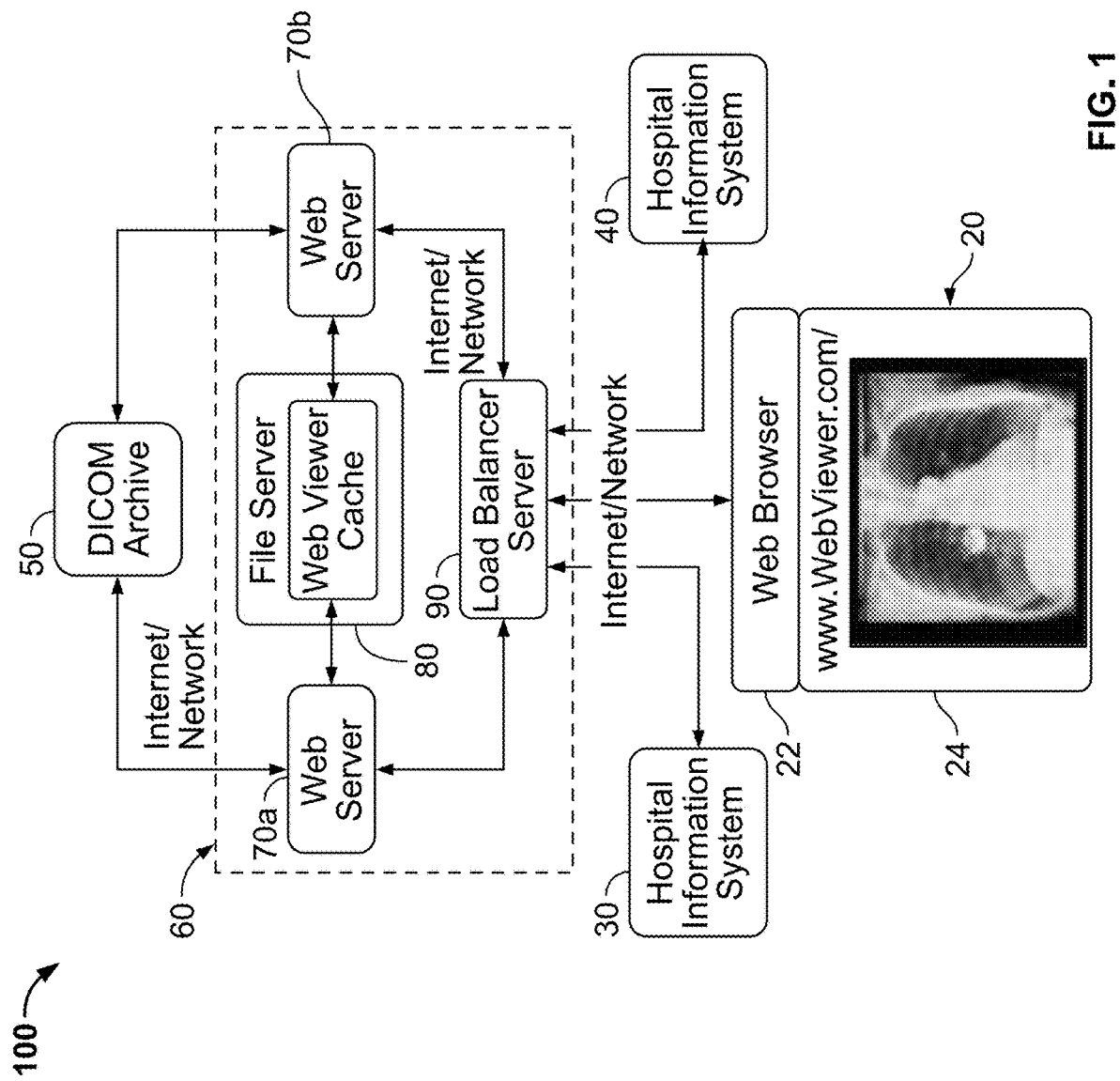
FIG. 1 is a block diagram depicting a system for viewing medical images, in accordance with an embodiment of the present specification.

The present specification is directed towards a system and method for viewing both pathology and radiology images in a web browser. In embodiments, the radiology images are represented in the DICOM standard format, whereas the pathology images are represented in a plurality of proprietary formats collectively known as Whole Slide Image (WSI) format. In embodiments, the pathology image representation format is first converted to a DICOM format and then stored in the system which enables viewing of the stored images via a web browser. In embodiments, the pathology images represented in WSI format are first converted into a pyramid representation format and subsequently converted to a DICOM format.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise", "include", "have", "contain", and forms thereof, are not necessarily limited to members in a list with which the words may be associated. Thus, they are intended to be equivalent in meaning and be open-ended in that an item or items following any one of these words is not meant to be an exhaustive listing of such item or items, or meant to be limited to only the listed item or items. It should be noted herein that any feature or component described in association with a specific embodiment may be used and implemented with any other embodiment unless clearly indicated otherwise.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred, systems and methods are now described.

As used in this specification, the conventional pathology image format or Whole Slide Image (WSI) format shall refer to each of the following file formats (referring to file extensions and their descriptions): .tiff as a single-file pyramidal tiled TIFF or BigTIFF with non-standard metadata; .sys as single-file pyramidal tiled with non-standard metadata and compression; .tif as single-file pyramidal tiled TIFF, with non-standard metadata and compression; .vms, .vmu, or .ndpi as multi-file JPEG/NGR with proprietary metadata and index file formats and single-file TIFF-like format with proprietary metadata; .scn as a single-file pyramidal tiled BigTIFF with non-standard metadata; .syslide as a SQLite database containing pyramid tiles and metadata; .mrxs as a multi-file with proprietary metadata and indexes; and .bif as a single-file pyramidal tiled BigTIFF with non-standard metadata and overlaps, or any other file format that complies with a conventional Whole Slide Image format.

Embodiments of the system of the present specification comprise a combination of web servers, a load balancer server, or a Kubernetes platform, a web viewer cache server, and a web browser accessible from one or more computers. The web browser, and thereby the embodiments, take advantage of some of the features of HTML 5, and provide for more efficient medical imaging viewing. In an embodiment, the web browser of the present system is functionally capable of rendering the images with a 'canvas' tag introduced in HTML 5 images. In an embodiment, the web server of the present system functions as a data processor that pre-processes medical images and stores the results in the web cache, which images may subsequently be transmitted using HTTP.

As used in this specification, the term "web cache" refers to a memory location (typically disk space local to a client device) where files, such as images, are stored in a format optimized for a web browser, such as a JPEG format. The storage is temporary and any such images will be deleted as needed, such as when a fixed amount of disk space has been reached and under a predefined rule, such as the first-in, first-out rule.

As used in this specification, the term "web archive" refers to a memory location (typically remote from a client device, such as in a cloud or network) where files, such as images, are stored persistently and preferably in a predefined format, such as a DICOM format. This memory location grows as needed and files, such as images, are deleted only when specifically requested by a user.

In embodiments, the system of the present specification provides both real time processing and pre-fetch processing of medical images by the web servers. In that regard, a load balancer server is provided in some embodiments to distribute and manage the work load performed by the one or more web servers to optimize processing, particularly in situations where there are numerous client-side users seeking access to the medical images stored in the system of the present specification. In some embodiments, the present specification employs a Kubernetes platform to distribute and manage the work load performed by the one or more web servers to optimize processing. The Kubernetes platform, as is known, is an open-source container orchestration platform that enables the operation of an elastic web server framework for cloud applications.

FIG. 1 is a block diagram depicting the system for viewing medical images, in accordance with an embodiment of the present specification. The system 100 comprises a client side system 10, a server side system 60, an image archive 50 coupled with the server side system 60 and a hospital information system (RIS) 40 and/or radiology information system (RIS) 40, and/or lab information system (LIS), also coupled with the server side system 60. Referring to FIG. 1, the client-side system 10 comprises one or more computers 20 comprising web browsers 22. In an embodiment, the web browsers 22 employ HTML 5 software and a monitor 24 for viewing medical images. In embodiments, the computers 20 may be comprised within or outside the HIS 30 or RIS 40 or LIS.

Through the use of computers 20 within or without the HIS 30 or RIS 40, requests for and access to stored images may be made through the use of server side system components 60. In some embodiments, the server side system components 60 comprise one or more web servers 70a, 70b, a web viewer cache server 80, which may be simply a file server on which viewer cache capabilities are programmed, and a load balancer server or a Kubernetes platform 90 to distribute and manage the work load performed by the one or more web servers 70a, 70b, to optimize processing. Connections between the individual components of the system components 60, and the connections between the computers 20 within or without the HIS 30 and RIS 40 or LIS, are made via one or more of numerous possible interfaces, such as a private network, a public network, and/or the Internet. The connection vehicle is not critical to functionality of embodiments of the present invention.

In an embodiment, the web browsers 22 load the data directly from the web viewer cache 80 and display them to the user locally. Hence, in embodiments, the web server (70a, 70b) is not involved functionally for user display. In embodiments, the web servers are configured to be accessed by multiple web browsers simultaneously, even when multiple servers are being employed in synchronous operation. In an embodiment, the web viewer cache 80 is also configured to detect the failure of any server being employed in data processing, and restart the processing steps handled by the failed server using another server.

In embodiments, the present system comprises multiple instances of the web server (70a and 70b) which are coordinated by the load balancer server or the Kubernetes platform 90. The instances of the web server share the common web viewer cache 80 which stores the result of the processing of both the radiology images and pathology images, optimized for viewing in the browser 22. The processed images are permanently stored in the image archive 50 in the DICOM format.

In various embodiments, the system 100 receives pathology images in WSI formats, or a plurality of other non-DICOM formats, and converts said images to a DICOM format prior to storing them in the image archive 50. The DICOM format allows storage of metadata regarding corresponding patients along with the images and is compatible with the picture archiving and communication system (PACS) enabling images in DICOM format to be stored and transmitted using commonly used DICOM devices, such as DICOM Archives, DICOM Routers and DICOM Viewers. In embodiments, the pathology images may be represented in a plurality of proprietary formats, which are collectively known as Whole Slide Image (WSI). As mentioned earlier, there are multiple file format in this category, such as but not limited to, .sys, .tif, .tiff, and .bif, among others.

In an embodiment, the system 100 processes the pathology images represented in the WSI format and converts said images to a pyramid representation, which is commonly used for viewing pathology images in a web browser, before converting said images to DICOM format. Since uncompressed pathology images are large, ranging typically from 3 Gb to 5 Gb, and are stored in different proprietary formats (WSI), it is difficult to view said images on a web browser using conventional means. Radiology images which are much smaller in size are downloaded entirely on a web browser for viewing. However, due to their large size, pathology images cannot be downloaded on a web browser entirely. Hence, the system of the present specification converts pathology images in proprietary WSI formats to a pyramid representation which enables only the portions of a pathology image at predefined resolutions desired to be viewed, to be downloaded on a web browser. The pyramid representation of pathology images involves organizing the data of a pathology image into multiple tiles/levels, wherein each tile/level comprises portions of the image at a predefined resolution.

Figure 2:
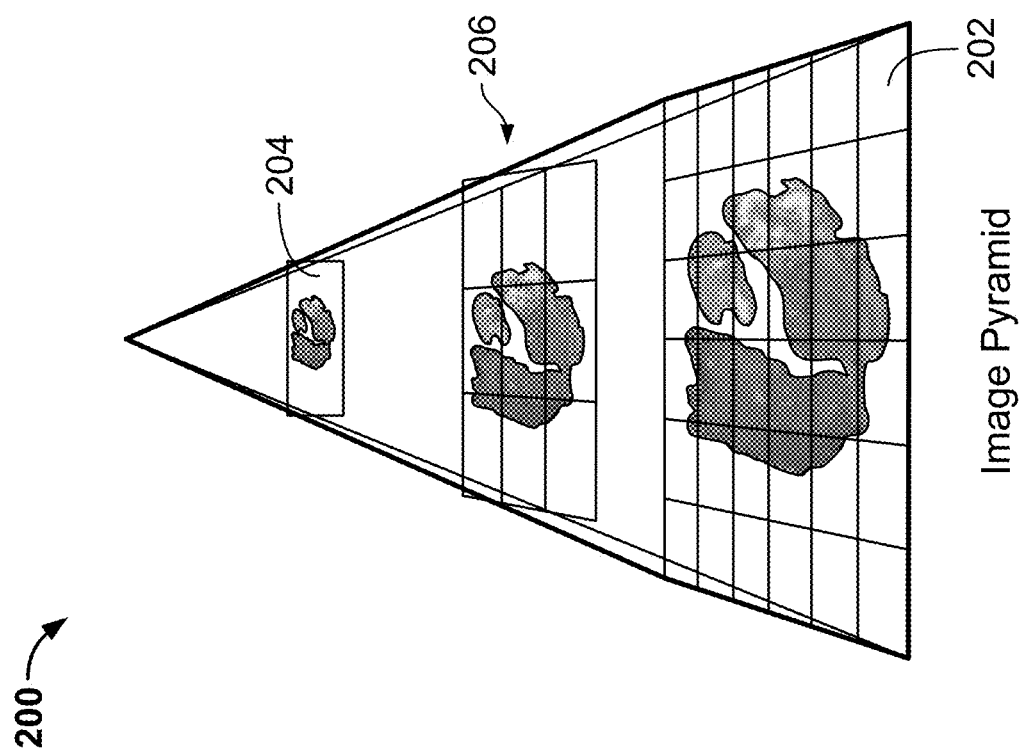
FIG. 2 illustrates a diagram of a pyramid representation of pathology images, in accordance with an embodiment of the present specification.

FIG. 2 illustrates a diagram of the pyramid representation of pathology images. In embodiments, a pathology image in WSI format is converted to a pyramid representation 200, wherein said representation enables said image to be stored at multiple levels of zoom or resolution. A base 202 of the pyramid 200 comprises a highest resolution representation of the pathology image, while a top 204 comprises a lowest resolution representation of the pathology image. In embodiments, the lowest resolution image is typically a thumbnail image, which is a very low-resolution version of the image, enabling a viewer to easily see the entire image. The pyramid representation 200 comprises a plurality of levels 206, wherein each level comprises the pathology image at an intermediate resolution which can be loaded onto a web browser when required for viewing. In embodiments, the base 200 or the bottom most level of the pyramid representation 200, comprises the image as it was acquired, meaning at the image's full resolution, while, each level above the base 200 comprises the image at half of the resolution in each dimension (one quarter of the resolution) of the previous level. In an embodiment, the pyramid representation 200 has at least two levels and a maximum of 100 levels.

Figure 3:
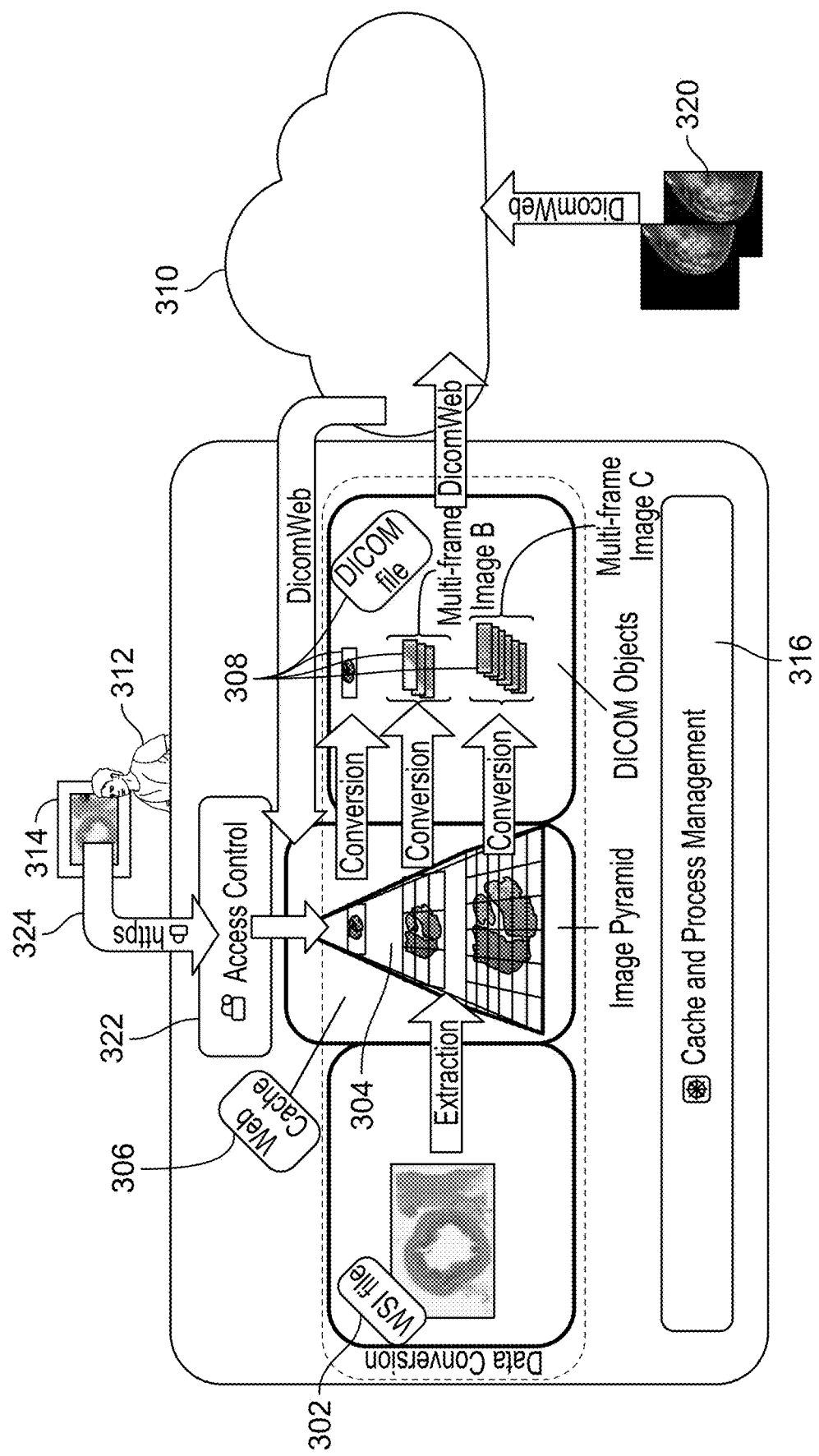
FIG. 3 is a flow diagram illustrating a process of converting pathology images to a DICOM format which may be accessed by a web browser for viewing, in accordance with an embodiment of the present specification.

In various embodiments, the system of the present specification enables easy viewing of pathology images via a web browser. FIG. 3 illustrates a flow diagram of the process of converting pathology images to the DICOM format which may be loaded on to a web browser for viewing, in accordance with an embodiment of the present specification. As shown in FIG. 3, a pathology image 302 is firstly converted into a pyramid representation 304 and stored in a web cache 306. Next, each level of the pyramid representation 304 comprising the image at a specific resolution is converted into an image represented in the DICOM format.

In embodiments, each level of the pyramid representation comprises a plurality of tiles, whereby each tile has pixel dimensions such as, but not limited to, 256×256, 512×512, or any increment within or from 128×128 to 2048×2048. In various embodiments, the tiles are typically images in a graphical format, such as a JPEG format. Since each level of a pyramid representation comprises different resolution levels of the same image, each level comprises a different number of tiles. In embodiments, each level of a pyramid representation is stored in a single DICOM file, and each tile is represented as a 'frame' in the DICOM file. In some embodiments, a DICOM file is a multiframe file storing multiple images in formats such as, but not limited to JPEG format. A pathology file converted into a pyramid representation is allotted a predetermined unique identification code known as a StudyUID. All of the images in DICOM files corresponding to the same pyramid representation are tagged with, or otherwise have associated therewith, the same StudyUID. Preferably, however, each level of images in the DICOM files has a different and unique SeriesUID code that is representative of the associated different resolution of the image. The bottom most level of the pyramid representation comprises the image as it was acquired, meaning at the image's full resolution, while, each level above the bottom level comprises the image at half of the resolution in each dimension (one quarter of the total resolution) of the previous level. In an embodiment, when the image resolution at a level becomes smaller than a predefined value, such as, for example less than half of a tile size, a next upper level of the pyramid representation may be generated by downsampling the previous level.

Hence the pyramid representation 304 is converted into a plurality of DICOM files 308, wherein the number of DICOM files 308 is equal to the number of levels in the pyramid representation 304, and each DICOM file 308 represents the image 302 at a specific, unique and predetermined resolution. The DICOM files 308 are stored in an image archive which may be a cloud based storage 310. A plurality of other images 320 in DICOM format, such as, but not limited to radiology images, may also be stored in the cloud based image storage 310. When a user 312 requests to view the image 302 at a specified resolution, the corresponding image (in jpeg format) from a corresponding DICOM file 308 is fetched from the cloud based storage 310 to the web cache 306, from where an access module 322 (such as a load balancer or a Kubernetes platform shown in FIG. 1) fetches said image by using the internet HTTPS protocol 324 for viewing by the user 312 in a web browser 314. The conversion, storage and fetching of the pathology image 302 for viewing in the web browser is managed by a cache and process management module 316 running in one or more web servers of the system of the present specification.

Figure 4A:
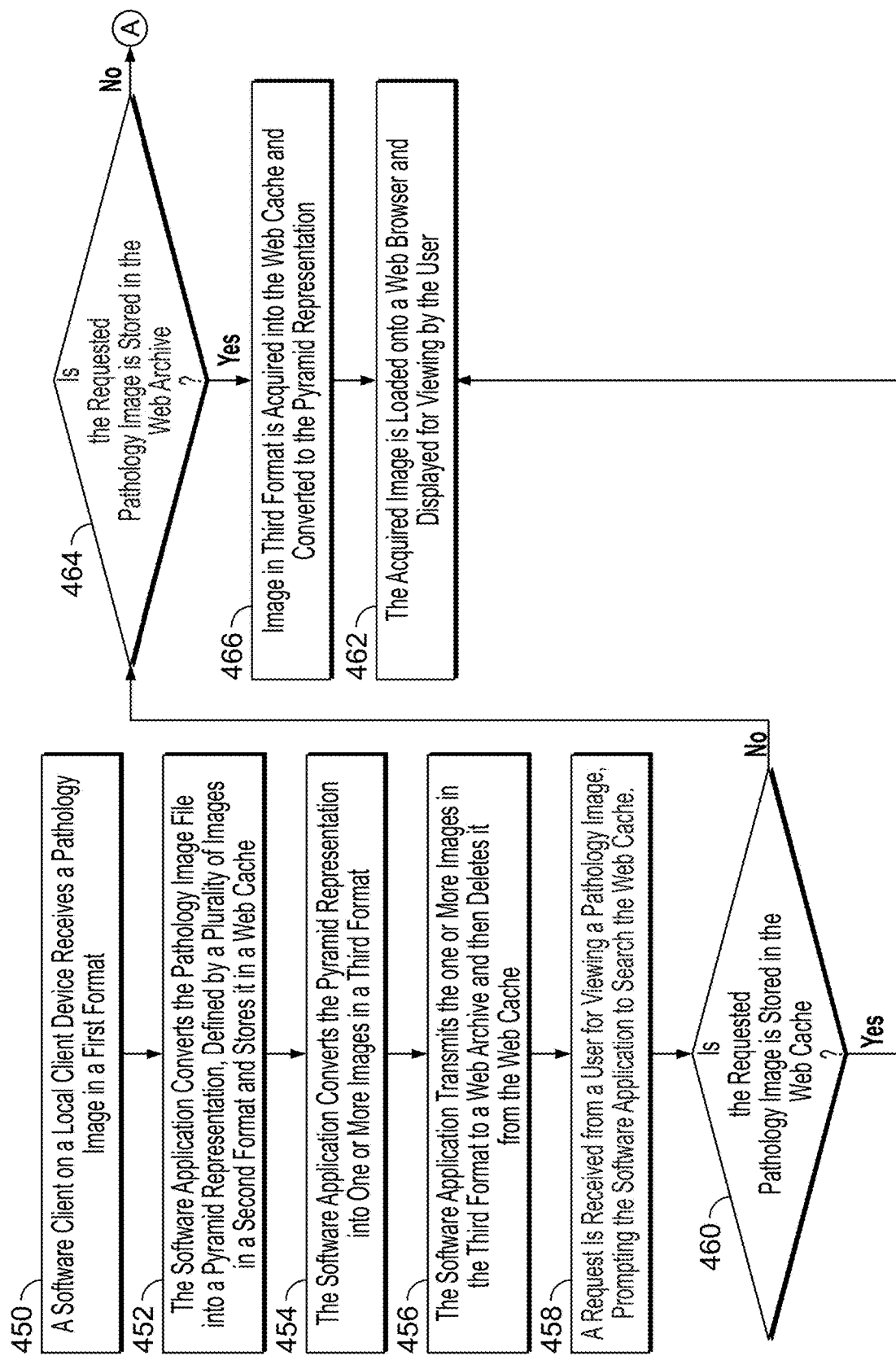
FIG. 4A is a flowchart describing a method of viewing pathology images via a web browser, in accordance with an embodiment of the present specification.

In some embodiments, as shown in FIG. 4A, at step 450, a software application on a local client device receives a pathology image, from a third party system, in a first format. Thus, a pathology image in a conventional first file format, such as WSI for example, is received by a software application executing in a client device with a browser. The software application is configured to access and manage a web cache local to the client device.

The software application converts, at step 452, the pathology image (in this case, the pathology image that is in the first file format, WSI) into a pyramid representation defined by a plurality of images in a second format which is stored in the web cache (which, in an embodiment, is a first memory). In embodiments, the second format may be a TIFF, JPEF, or PNG format, for example. In the software application, at step 454, the pyramid representation is converted to one or more image files in a third format, wherein the third format may be a DICOM format. The software application transmits, at step 456, the one or more images in the third format (for example, DICOM format) to a web archive (which, in an embodiment, is a second memory), and then deletes it from the web cache. Thus, the software application causes the file, which is in a pyramid representation, to be deleted from the web cache after it has been stored in the web archive in the form of one or more files in a third format (for example, DICOM format).

When the user requests the study corresponding to the pathology image at step 458, the software application searches the web cache. If, at step 460, it is determined that the study is present in the web cache, the software application causes the web browser to display the study/pathology image at step 462. If a pathology image/study requested by a user via the software application is not in the web cache, at step 464, the software application will access the web archive and acquire the corresponding one or more image files in the third format (for example, DICOM format) into the web cache. At step 466, the acquired one or more image files in the third format (for example, DICOM format) that are now in the web cache are converted it to the pyramid representation in the web cache, as described above, for display via the web browser, such as at step 462.

Figure 4B:
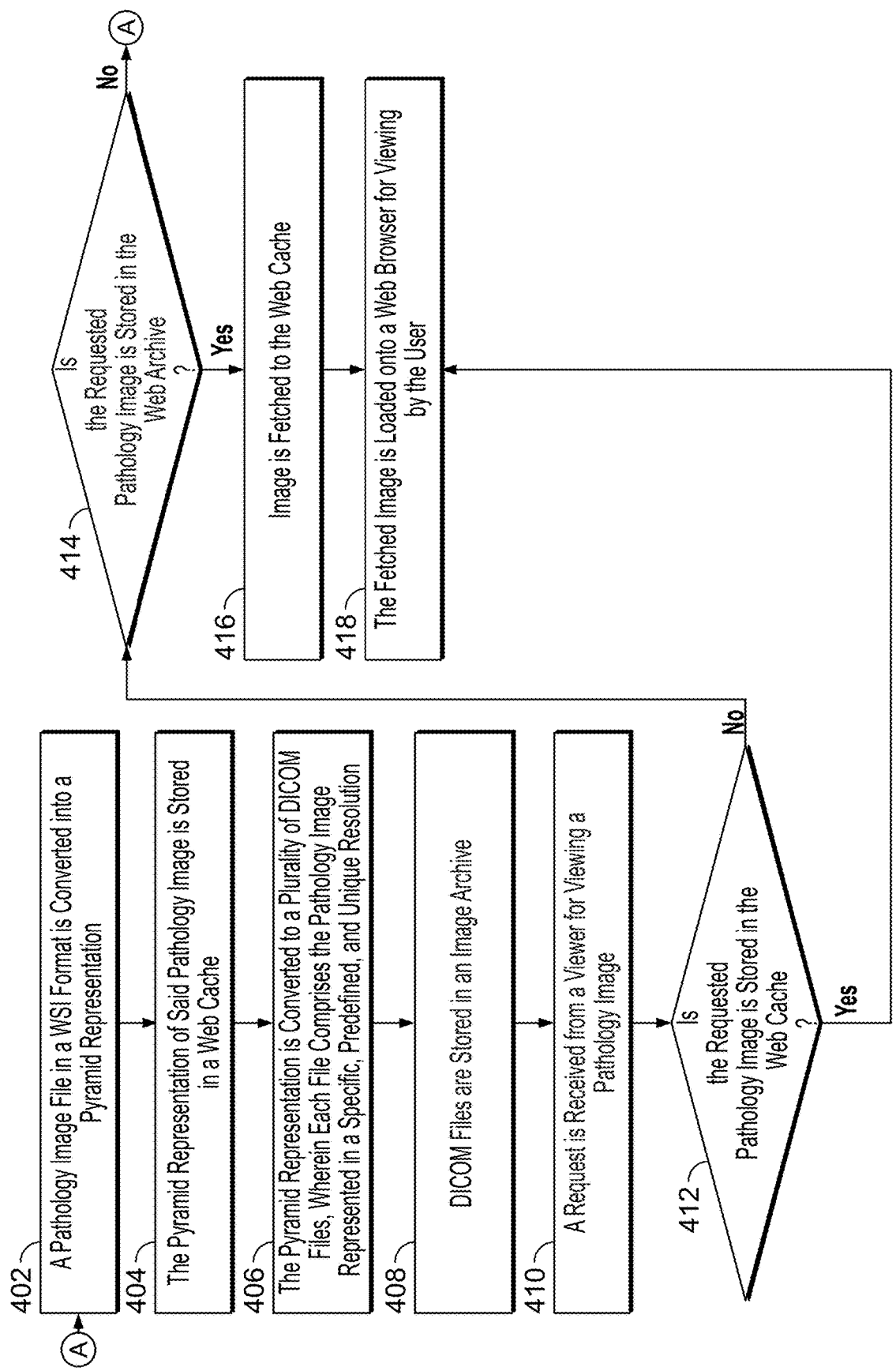
FIG. 4B is a flowchart describing another method of viewing pathology images via a web browser, in accordance with an embodiment of the present specification.

FIG. 4B is a flowchart depicting another method of viewing pathology images via a web browser, in accordance with an embodiment of the present specification. At step 402 a pathology image file in a WSI format is converted into a pyramid representation. The pyramid representation comprises a plurality of levels, wherein each level comprises the pathology image file stored in a predefined unique resolution, and wherein a bottom most level of the pyramid comprises said file represented in a highest resolution, the top most level of the pyramid comprises said file represented in a lowest resolution and intermediate levels comprise said file in a plurality of intermediate resolutions arranged in an ascending order from top to bottom level of the pyramid representation. In embodiments, one or more web servers of the system of the present specification, such as shown in FIG. 1 converts the pathology image file in a WSI format into a pyramid representation, by using parameters such as, but not limited to, a size and format of each level of the pyramid. In some embodiments, the format may be a JPEG format.

At step 404 the pyramid representation of said pathology image is stored in a web cache of the system of the present specification. In an embodiment the web cache is as shown in FIG. 1. At step 406 each image, which is in a first format and represents a specific, different resolution level of the pyramid representation, is converted into a corresponding image in a DICOM format. In an embodiment, the first format is a WSI format. In other embodiments, the first format may be of any format type. In some embodiments, the first format may be in a DICOM format wherein the DICOM format files do not contain all of the levels of the pyramid; the tile size used in the DICOM files is not optimal for viewing (too large or too small); or the format of the images in the DICOM format files are not optimal for viewing, for example if the format is an uncompressed format such as, but not limited to, TIFF. Hence, the entire pyramid representation of a single WSI image is converted to a plurality of DICOM files, wherein each DICOM file comprises at least one of the pyramid levels of the pathology image that corresponds to a specific, predefined, and unique resolution. In embodiments, one or more web servers of the system of the present specification, such as is shown in FIG. 1 converts the pyramid representation into the plurality of DICOM files. Hence, in embodiments, step 406 comprises converting the pathology image into a pyramid representation file comprising a plurality of levels, wherein each of the plurality of levels corresponds to the image at a different degree of resolution, and wherein each level stores the image in a second format at a different degree of resolution; and storing the pyramid representation file in a web cache. In various embodiments, the second format may be a DICOM image format, such as, but not limited to TIFF, JPEG, and PNG.

At step 408 the plurality of DICOM files are stored in an image archive comprising other DICOM files representing other images such as pathology images and radiology images. In embodiments, the image archive stores images in the pyramid format and the corresponding DICOM files are deleted. In embodiments, the image archive comprises pyramid files comprising multiple levels of DICOM images, wherein each of the pyramid levels has a predetermined size with a predetermined specific encoding, such as but not limited to TIFF, JPEG, and PNG.

Stated differently, in one embodiment, a pathology image in a conventional file format, such as WSI is received by a software application executing in a client device with a browser. The software application is configured to access and manage a web cache local to the client device. The software application converts the WSI formatted file into a pyramid representation with images, as described above, that are in a TIFF, JPEF, or PNG format and which is stored in the web cache. The software application transmits the file, which is in a pyramid representation, to a web archive. At the web archive or in the software application (prior to transmission), the pyramid representation is converted to one or more files in a DICOM format. The software application causes the file, which is in a pyramid representation, to be deleted from the web cache after it has been stored in the web archive in the form of one or more files in a DICOM format. If a study requested by a user via the software application is not in the web cache, the software application will access the web archive, request the corresponding one or more files in a DICOM format, receive the one or more files in a DICOM format, and convert it to the pyramidal representation, as described above, for display via the web browser.

At step 410 a request is received from a viewer for viewing a pathology image. In embodiments, the received request is for viewing a pathology image at a specified resolution. At step 412 it is determined if the requested pathology image is stored in the web cache. At step 414 if the requested pathology image is not stored in the web cache, it is determined if the requested pathology image is stored in the image archive. If requested pathology image is not stored in the web cache and if the requested pathology image is stored in the image archive, said image is fetched to the web cache at step 416. In embodiments, step 416 comprises extracting the pyramid levels/tiles, which are stored as frames in JPEG format in the image archive, and storing the extracted images in the web cache as JPEG images, enabling efficient access to said images by the browser. In an embodiment, step 416 comprises loading the image in the second format (for example, TIFF, JPEG, and PNG) corresponding to the specified resolution onto a web browser that is in data communication with the web cache.

In embodiments, a load balancer server or a Kubernetes platform and one or more web servers, as shown in FIG. 1 enables fetching the requested pathology image from the web cache or the image archive. If the requested pathology image is not stored in the image archive or the web cache, then the requested pathology image file in a WSI format is converted into a pyramid representation at step 402 and steps 402 to 416 are carried out. At step 418 the fetched image is loaded onto a web browser for viewing by the user.

In an embodiment, the web cache has a maximum size, and once it exceeds that capacity, a clean-up process would preferably automatically analyze all the data in the Web Cache and remove some of it. At any image viewing request received by the web browser the list of DICOM images processed and available on the web cache is sent to the web browser via the load balancer or the Kubernetes platform, and/or one or more web servers, as shown in FIG. 1. The web server(s) indicates to the web browser if the processing is completed or not. In a case where the processing of the requested pathology image is not complete, the web browser will typically re-request the image information in few seconds until it receives the indication that the processing is complete and the image is available for viewing in the web browser.

In various embodiments, the method of the present specification allows image data in WSI format to be converted in a web cache so that the image is immediately available to a user for viewing. Since, the web cache has a limited memory, the pathology images converted to DICOM format are stored in an image archive for long term storage, so that even the images evicted from the web cache may be retrieved from the image archive to the web cache and be made available for viewing in a web browser.

The above examples are merely illustrative of the many applications of the system and method of the present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

What is claimed is:

1. A system adapted to enable a user to view one or more pathology images in a web browser, wherein the system comprises:
   one or more web servers, wherein the one or more web servers is configured to:
      obtain at least one of the one or more pathology images in a first format;
      convert the pathology image into a file comprising images grouped into a plurality of levels, wherein the images in different ones of the plurality of levels correspond to a portion of the pathology image at a different degree of resolution, wherein each image in a given one of the plurality of levels corresponds to a portion of the pathology image at a same degree of resolution, and wherein the images are in a second format;
      cause the file to be stored in a first memory;
      convert the images into a third format; and
      cause the images to be stored in the third format in a second memory, wherein the third format is different from the second format and the first format; and
   a plurality of programmatic instructions adapted to be stored in non-transient memory and executed on a client device, wherein, when executed, the plurality of programmatic instructions are adapted to receive a request from the user to view the pathology image and load one or more of the images from at least one of the plurality of levels corresponding to a specified resolution and wherein the one or more images are in the second format.

2. The system of claim 1, wherein the file is in a hierarchical representation.

3. The system of claim 1, wherein the file is in a pyramid representation.

4. The system of claim 1, wherein the one or more web servers is configured to convert the images into a third format such that the images' degrees of resolution are maintained.

5. The system of claim 1, wherein the plurality of programmatic instructions are adapted to receive the request identifying the specified resolution.

6. The system of claim 1, wherein the first memory comprises a web cache in the client device.

7. The system of claim 1, wherein the second memory comprises a web archive.

8. The system of claim 1, wherein the first format is a WSI format.

9. The system of claim 1, wherein the second format is at least one of a TIFF format, a JPEG format, or a PNG format.

10. The system of claim 1, wherein the third format is a DICOM format.

11. The system of claim 1, wherein the file is in a pyramid representation and wherein a number of the plurality of levels in the pyramid representation file is at least two.

12. The system of claim 1, wherein the file is in a pyramid representation and wherein a number of the plurality of levels in the pyramid representation file is no greater than one hundred.

13. The system of claim 1, wherein the file is in a pyramid representation and wherein a top of the plurality of levels in the pyramid representation file comprises the pathology image at a lowest resolution.

14. The system of claim 1, wherein the file is in a pyramid representation and wherein a base of the plurality of levels in the pyramid representation file comprises the pathology image at a highest resolution.

15. The system of claim 1, wherein the client device is remote from the one or more web servers.

16. The system of claim 1, wherein the plurality of programmatic instructions are adapted to load the one or more images into the web browser.

17. The system of claim 1, wherein the web browser is coupled with the first memory.

18. A system adapted to enable a user to view one or more pathology images in a web browser, wherein the system comprises:
   one or more web servers, wherein the one or more web servers is configured to:
     obtain at least one of the one or more pathology images in a first format;
     convert the pathology image into a file comprising images grouped into a plurality of levels, wherein the images in different ones of the plurality of levels correspond to a portion of the pathology image at a different degree of resolution, wherein each image in a given one of the plurality of levels corresponds to a portion of the pathology image at a same degree of resolution, and wherein the images are in a second format;
     cause the file to be stored in a first memory;
     convert the images into a third format; and
     cause the images to be stored in the third format in a second memory, wherein each of the first format, second format and third format is different from each other; and
   a plurality of programmatic instructions adapted to be stored in non-transient memory and executed on a client device, wherein, when executed, the plurality of programmatic instructions are adapted to receive a request from the user to view the pathology image and load one or more of the images from at least one of the plurality of levels corresponding to a specified resolution and wherein the one or more images are in the second format.

19. The system of claim 18, wherein the file is in at least one of a hierarchical representation or a pyramid representation.

20. The system of claim 18, wherein the one or more web servers is configured to convert the images into a third format such that the images' degrees of resolution are maintained.

21. The system of claim 18, wherein the plurality of programmatic instructions are adapted to receive the request identifying the specified resolution.

22. The system of claim 18, wherein the first memory comprises a web cache in the client device.

23. The system of claim 18, wherein the second memory comprises a web archive.

24. The system of claim 18, wherein the first format is a WSI format.

25. The system of claim 24, wherein the second format is at least one of a TIFF format, a JPEG format, or a PNG format.

26. The system of claim 25, wherein the third format is a DICOM format.

27. The system of claim 18, wherein the file is in a pyramid representation and wherein a number of the plurality of levels in the pyramid representation file is at least two.

28. The system of claim 18, wherein the file is in a pyramid representation and wherein a number of the plurality of levels in the pyramid representation file is no greater than one hundred.

29. The system of claim 18, wherein the file is in a pyramid representation and wherein a top of the plurality of levels in the pyramid representation file comprises the pathology image at a lowest resolution.

30. The system of claim 18, wherein the file is in a pyramid representation and wherein a base of the plurality of levels in the pyramid representation file comprises the pathology image at a highest resolution.

* * * * *